(12) United States Patent
Cook et al.

(10) Patent No.: US 9,042,993 B2
(45) Date of Patent: May 26, 2015

(54) SKIN-HAIR TREATMENT METHOD AND SYSTEM

(71) Applicant: Proventure (Far East) Limited, Hong Kong (HK)

(72) Inventors: Stuart A. Cook, Duluth, GA (US); Bruno Gimelli, Zollikofen (CH); James N. Doyle, Jr., Westlake, OH (US)

(73) Assignee: Proventure (Far East), Limited, Central (HK)

( * ) Notice: Subject to any disclaimer, the term of this patent is extended or adjusted under 35 U.S.C. 154(b) by 0 days.

(21) Appl. No.: 14/173,428

(22) Filed: Feb. 5, 2014

(65) Prior Publication Data

US 2014/0155976 A1    Jun. 5, 2014

Related U.S. Application Data

(63) Continuation of application No. 11/876,624, filed on Oct. 22, 2007, now Pat. No. 8,655,448, which is a continuation of application No. 10/879,804, filed on Jun. 29, 2004, now Pat. No. 7,305,269, which is a continuation-in-part of application No. 10/268,401, filed on Oct. 10, 2002, now Pat. No. 6,766,199.

(51) Int. Cl.
*A61N 1/04* (2006.01)
*A61H 7/00* (2006.01)
*A61N 1/32* (2006.01)

(52) U.S. Cl.
CPC .............. *A61N 1/0408* (2013.01); *A61H 7/003* (2013.01); *A61H 2201/0153* (2013.01);
(Continued)

(58) Field of Classification Search
CPC .................. A61H 2201/0153; A61H 2201/10; A61H 2201/1604; A61H 2201/1685; A61H 2205/021; A61H 2205/022; A61H 7/003; A61H 1/328

USPC ................... 607/2, 3, 50, 115, 150–151, 153; 600/19–20

See application file for complete search history.

(56) References Cited

U.S. PATENT DOCUMENTS

| 3,424,165 A | 1/1969 | Moss |
| 4,153,726 A | 5/1979 | Borggrefe et al. |

(Continued)

FOREIGN PATENT DOCUMENTS

WO    90/04997    5/1990

*Primary Examiner* — Rex R Holmes
(74) *Attorney, Agent, or Firm* — Fulwider Patton LLP

(57) ABSTRACT

A method and system of conditioning human skin and hair using a hand-held skin/hair conditioner having interchangeable interface conductors that are contoured to enhance electrical conductivity between the conditioner and a variety of body areas. Each of the interchangeable interface conductors are preferably formed to maximize surface area contact with a variety of body surfaces such as scalp/hair, body skin, and facial skin. In a preferred embodiment, the skin/hair conditioner is formed to fit comfortably and controllably in a user's grasp while providing maximum contact with the selected body surface. The skin/hair conditioner includes an audio signal generator and a vibration mechanism to alert a user of a change in status of the conditioner. The interface conductors may be (1) smoothly rounded, (2) include teeth, (3) spherical or hemispherical (4) include multiple rounded nodules. The housings for the conditioner may be (1) elongated and somewhat flattened, (2) of elongated cylindrical shape, or (3) of a compact configuration similar to a door knob. The interface conductors and conditioning system may have a releasable latch, and spring arrangements for ejecting the interface conductor when the latch is released.

5 Claims, 9 Drawing Sheets

(52) U.S. Cl.
CPC .... *A61H 2201/10* (2013.01); *A61H 2201/1604* (2013.01); *A61H 2205/021* (2013.01); *A61H 2205/022* (2013.01); *A61N 1/328* (2013.01); *A61H 2201/1685* (2013.01)

(56) References Cited

U.S. PATENT DOCUMENTS

| | | | |
|---|---|---|---|
| 4,323,073 A | 4/1982 | Ferris | |
| 4,590,069 A | 5/1986 | Deckner et al. | |
| 4,760,096 A | 7/1988 | Sakai et al. | |
| 4,847,083 A | 7/1989 | Clark | |
| 4,975,218 A | 12/1990 | Rosser | |
| 5,069,211 A | 12/1991 | Bartelt et al. | |
| 5,251,637 A | 10/1993 | Shalvi | |
| 5,385,530 A * | 1/1995 | Wu | 601/21 |
| 5,514,167 A | 5/1996 | Smith et al. | |
| 5,607,461 A | 3/1997 | Lathrop | |
| 5,879,323 A | 3/1999 | Henley | |
| RE36,260 E | 7/1999 | Smith et al. | |
| 5,931,859 A * | 8/1999 | Burke | 607/66 |
| 5,995,869 A | 11/1999 | Cormier et al. | |
| 6,007,502 A | 12/1999 | Lee | |
| 6,026,327 A * | 2/2000 | Dervieux | 607/46 |
| 6,079,103 A | 6/2000 | Melton et al. | |
| 6,119,038 A | 9/2000 | Cook | |
| 6,162,219 A | 12/2000 | Nilsson et al. | |
| 6,385,487 B1 | 5/2002 | Henley | |
| 6,687,537 B2 | 2/2004 | Bernabei | |
| 6,766,199 B2 * | 7/2004 | Cook et al. | 607/50 |
| 7,305,269 B2 * | 12/2007 | Cook et al. | 607/50 |
| 8,655,448 B2 * | 2/2014 | Cook et al. | 607/50 |
| 2002/0147466 A1 * | 10/2002 | Bernabei | 607/3 |

* cited by examiner

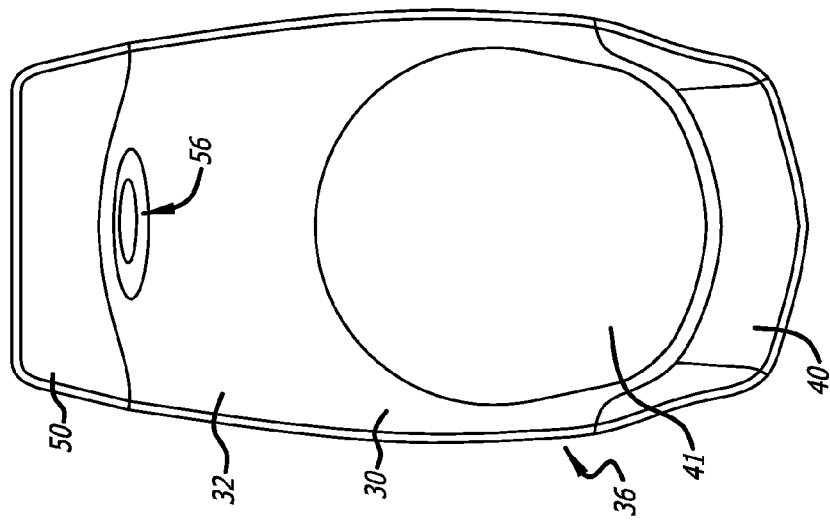
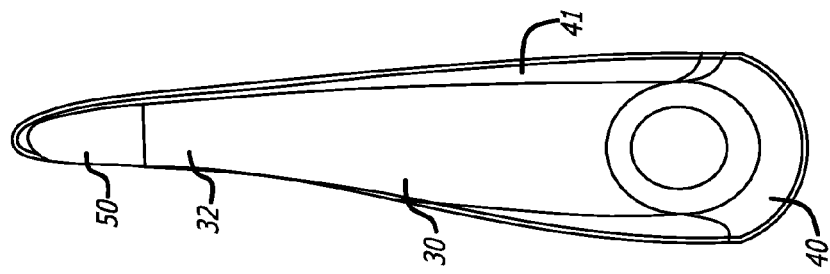
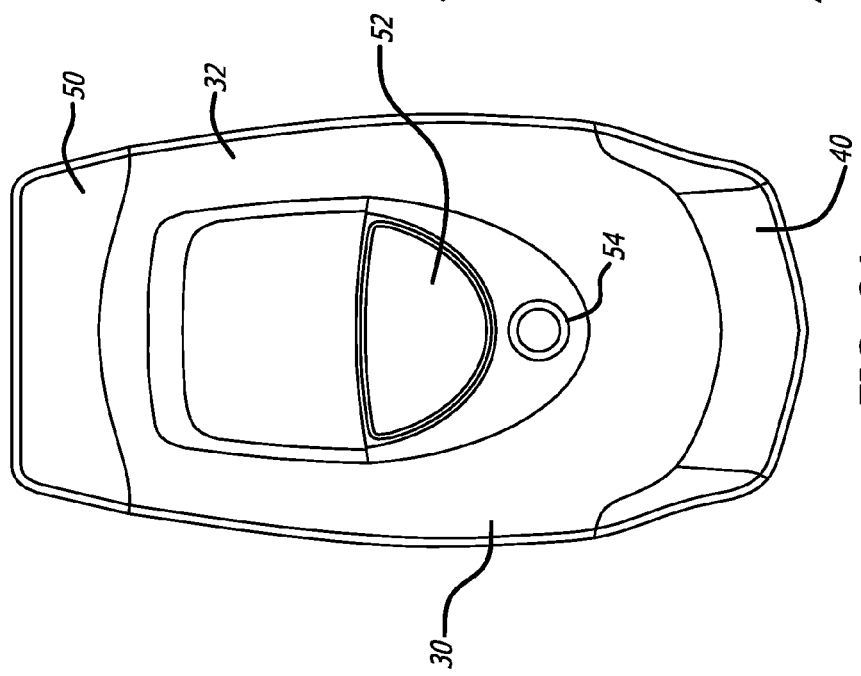

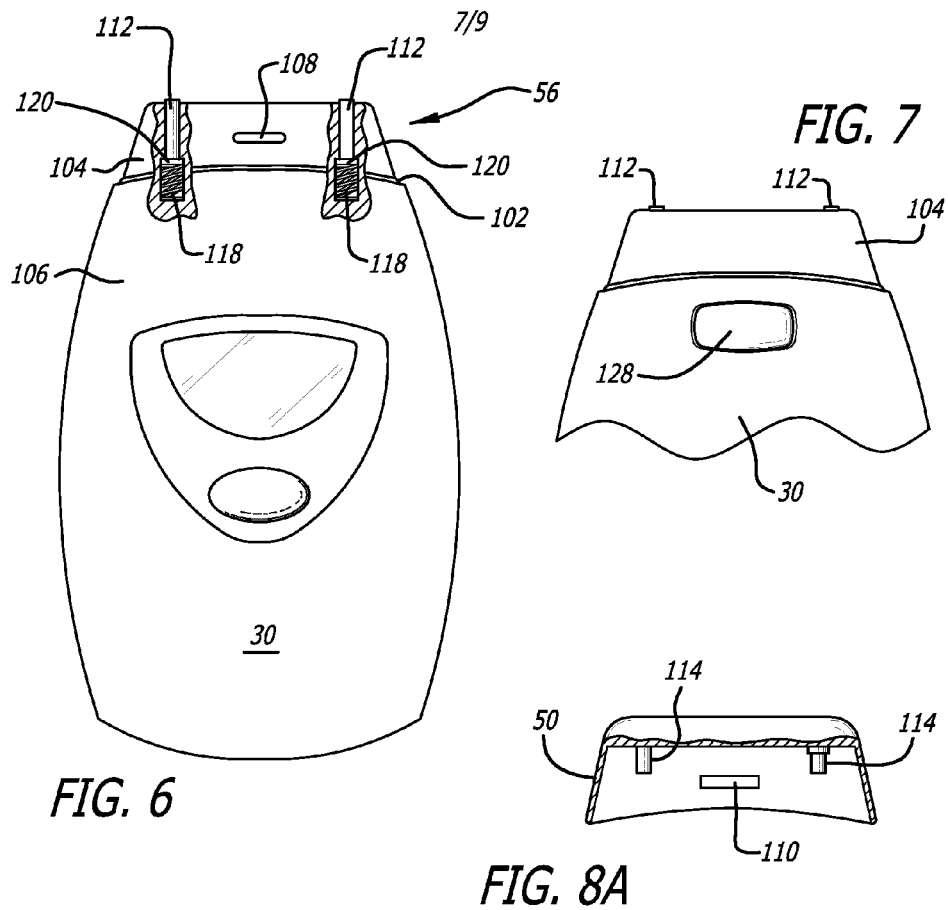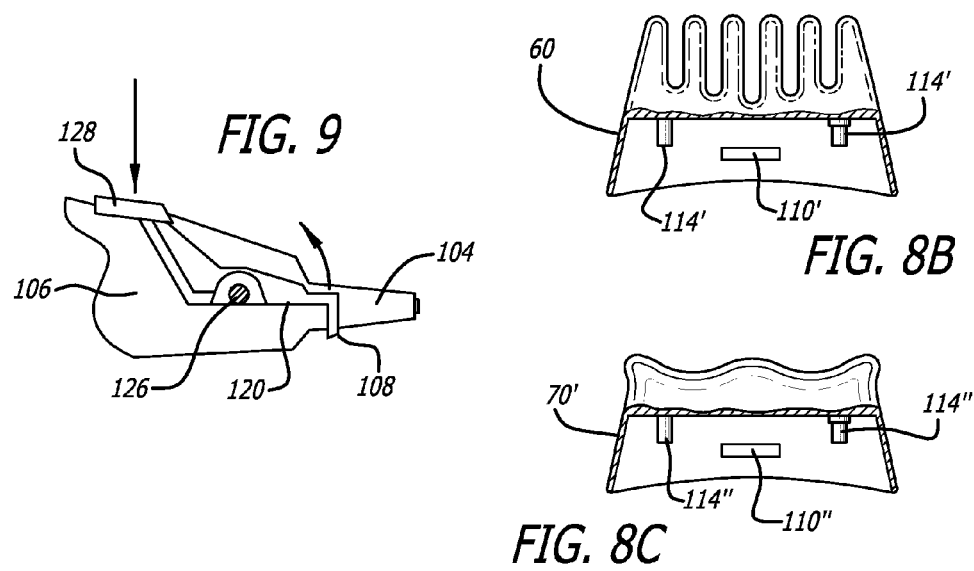

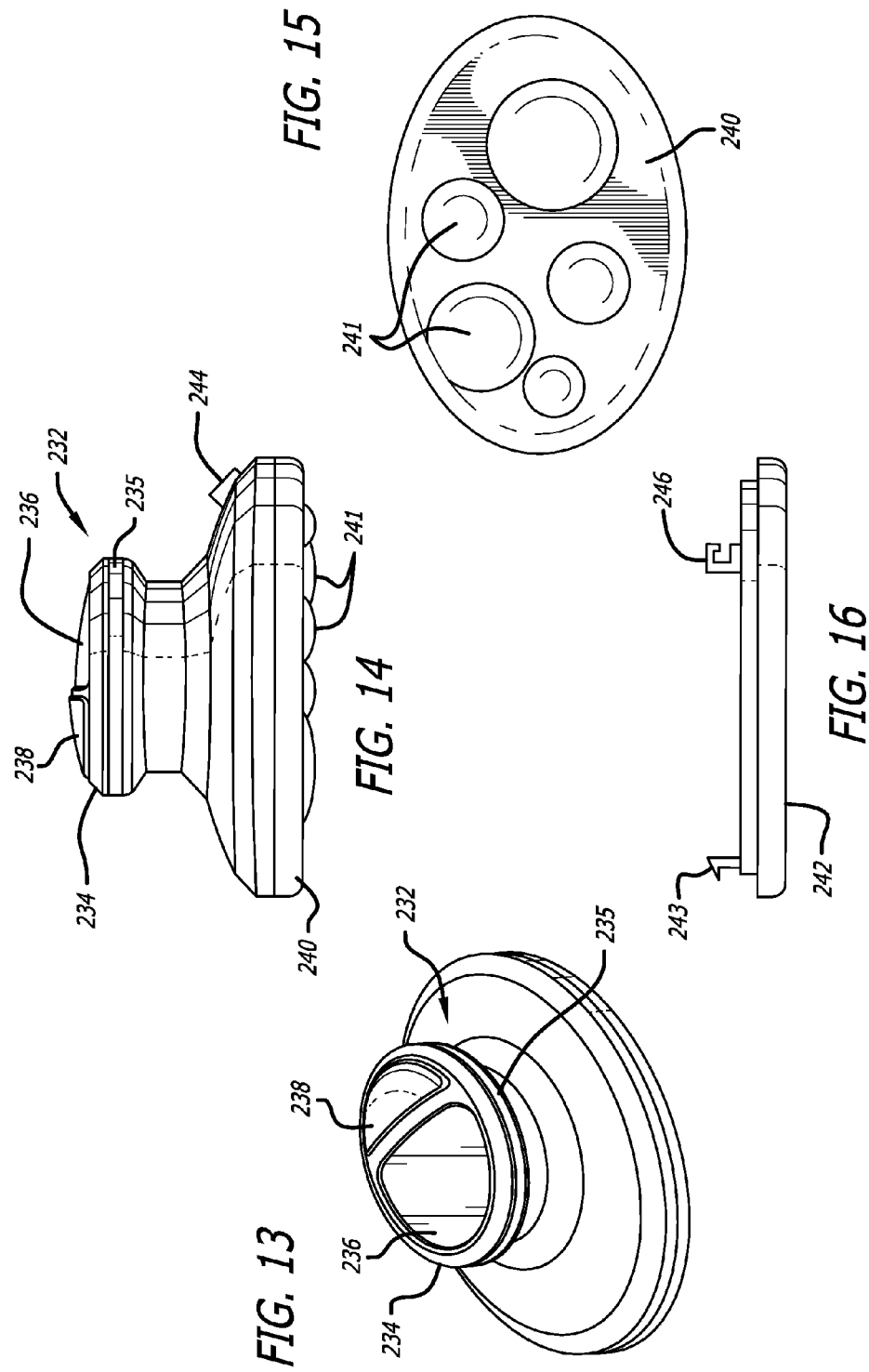

SKIN-HAIR TREATMENT METHOD AND SYSTEM

CROSS-REFERENCE TO RELATED APPLICATION

This application is a continuation of U.S. patent application Ser. No. 11/876,624, filed 22 Oct. 2007, now U.S. Pat. No. 8,655,448, which is a continuation of U.S. patent application Ser. No. 10/879,804, filed 29 Jun. 2004, now U.S. Pat. No. 7,305,269, issued 4 Dec. 2007, which is a continuation-in-part of U.S. patent application Ser. No. 10/268,401, filed 10 Oct. 2002, now U.S. Pat. No. 6,766,199, issued 20 Jul. 2004, incorporated by reference.

BACKGROUND OF THE INVENTION

1. Field of the Invention

This invention relates to treatment of human skin and hair, and more particularly to method and system of conditioning human skin and hair using a conditioner on it having interchangeable conducting heads and/or conditioner units selected for use in the treatment of selected areas of the anatomy.

2. Description of Related Art

A variety of methodologies have been pursued to improve human skin treatments that enhance skin appearance. One particular treatment includes the application of safe, low-levels of current to human skin in conjunction with topical preparations such as skin cleansers and moisturizers. Several hand-held devices have been used in the past to apply low-level electrical current to the skin.

For example, U.S. Pat. No. 5,514,167 describes a hand holdable skin treatment apparatus that applies a small charge of electrical energy to selected contours of the face and neck. The skin treatment apparatus includes a housing containing a battery powered circuit. A pair of spaced apart electrical conductors are mounted on the exterior of the housing. During operation, one of the conductors is in continuous contact with the user's hand while the other conductor is horseshoe shaped and applied to the skin to be treated.

Another example is U.S. Pat. No. 6,119,038 that is directed to a skin treatment system and method using a hand-held electric skin/hair conditioner, an alkaline pH pretreatment, and an acidic pH treatment. The hand-held conditioner includes a housing containing electrical circuitry including a microprocessor and a rechargeable battery, an alphanumeric display coupled with the microprocessor, and two external broad area conductive electrodes connected to the circuitry. The treatment unit also includes recharging terminals for use with a recharger assembly. One of the electrodes, a hand-engaging electrode, is adapted to be in continuous contact with a user's hand during use, and the other electrode, a skin electrode, is adapted to apply electrical current to the skin of the user. The method includes applying the pretreatment to clean skin, holding the skin electrode to the cheek, moving the skin electrode over the skin to be treated while transmitting negative and positive current flow, washing the treated skin, applying the treatment to the skin, and moving the skin electrode over the skin to be treated.

Although the aforementioned skin treatment devices are useful for applications to facial skin, treatment of other areas of the body, such as scalp/hair and body skin, is desirable. Numerous health care and beauty care products have been developed for facial skin therapy, but many products have also been developed for application to other areas of the body. What is needed is a skin/hair treatment unit for use with a variety of body surfaces such as scalp/hair, body skin, and facial skin. Additionally needed is a skin/hair treatment unit having a hand engaging electrode that is optimally positioned to enhance conductivity to the face skin, body skin, and scalp/hair. Further needed is a skin/hair treatment system with a treatment unit having simple and easy interchangeable interfaces to address a variety of body surfaces.

SUMMARY OF THE INVENTION

An object of this invention is to provide a skin/hair treatment unit for use with a variety of body surfaces such as scalp/hair, body skin, and facial skin.

Another object of this invention is to provide a skin/hair treatment unit having a hand engaging electrode that is optimally positioned to enhance conductivity to the face skin, body skin, and scalp/hair.

A further object of this invention is to provide a skin/hair treatment system with a treatment unit having simple and easy interchangeable interfaces to address a variety of body surfaces.

A more particular object of this invention is to provide a skin/hair treatment system having a hand-held treatment unit with interchangeable interface conductors, each of which are optimally shaped for use with a variety of body surfaces.

Another more particular object of this invention is to provide a skin/hair treatment system having a hand-held treatment unit with device ergonomics that increase the ability of the user to adequately hold the unit under various adverse conditions.

Another object of this invention is to provide a skin/hair treatment method for application to a variety of body surfaces including body skin, scalp/hair, and facial skin.

These and other objects of the invention are accomplished by providing a hand-held skin/hair conditioner having at least one interchangeable interface conductor that is attachable to the conditioner and electrically coupled with the conditioner. The skin/hair conditioner also includes a housing having a front end and a hand-engaging surface, a front end electrode connected to the front end of the housing, a hand-engaging electrode connected to the hand-engaging surface of the housing, a power source contained within the housing, an electrical system connected to the power source, the hand-engaging electrode, and the front electrode for controlling current supplied to the hand-engaging electrode and the front end electrode.

These and other objects of the invention are also accomplished by providing a skin/hair conditioning system having a topical water-based pretreatment preparation with negatively charged ions, a topical water-based treatment preparation with positively charged ions, and the aforementioned hand-held skin/hair conditioner.

These and other objects of the invention are also accomplished by providing a method of conditioning human skin/hair by selecting an interchangeable interface conductor for a hand-held conditioner based on an application to a body area, pretreating the body area with a negatively charged ionic pretreatment preparation, operate the hand-held conditioner in contact with the pretreatment preparation and the body area, removing the pretreatment preparation, treating the body area with a positively charged ionic treatment preparation, operating the hand-held conditioner in contact with the treatment preparation and the body area and removing excess acidic treatment, if necessary.

Other shortcomings and differences between the present invention and the prior art including the Henley U.S. Pat. No. 5,879,323 and the Lathrop U.S. Pat. No. 5,607,461, include (1) the location of the hand electrode toward the middle of the unit, (2) the Lathrop device has no hand electrode and the electric current merely flows between the two electrodes, (3) the lack of broad area smoothly rounded electrodes for (4) massaging the applicator electrode over an extended area of the hair or skin, (5) selectively providing positive or negative current flow, (6) selecting lotions, creams or gel to match the selected area of the anatomy and the applicator electrode, and (7) the system includes arrangements for matching the electrical current flow, polarity, and treatment time for the selected area to be treated.

A key element of any skin treatment is deep penetration. By the present invention our skin conditioner assembly achieves this desired deep penetration by the following:

(A) Mechanical compatibility between the applicator electrode configuration and the area of the body to be treated.

(B) Electrical current flow through the body and through the treatment area, which current flow carries the treatment material deep into the skin.

(C) Interchangeable applicator electrodes with different configurations, so that a single basic unit may provide mechanical and electrical compatibility with the part of the body selected for treatment.

It may also be noted that the housing or an overall configuration of the galvanic treatment unit may take different forms particularly adapted for treatment of different parts of the body. Thus, the unit shown in FIGS. 1 through 4 and 6 is somewhat flattened and elongated; the form of the unit of FIGS. 10 and 11 is cylindrical; and that of the unit of FIGS. 13 and 14 is of a flattened oval configuration somewhat resembling a door knob.

Accordingly, the multi-purpose functionality provides a completely novel system with many factors coordinated toward the selected treatment area, including the shape of the conditioning unit, the conforming electrode configuration, the direction of body current flow, timing, type of treatment lotion, cream or gel, all conforming to the desired type of treatment and selected treatment area of the anatomy.

Other objects, features and advantages of the invention will become apparent for a consideration of the following detailed description, and from the associated drawings.

BRIEF DESCRIPTION OF THE DRAWINGS

FIG. 2A is a top view of a skin/hair conditioner with a standard interface conductor 50 attached thereto in accordance with one embodiment of the present invention;

FIG. 2B is a side view of the skin/hair conditioner shown in FIG. 2A;

FIG. 2C is a bottom view of the skin/hair conditioner shown in FIG. 2A;

FIG. 6 is a front view of one side of the conditioner, showing the retractable latch and the spring-loaded quick release construction;

FIG. 7 is a view of the other side of the unit with the release button area shown;

FIGS. 8A, 8B and 8C are cut-away views of the interface conductors or applicators with the inner guide pins and latch recess shown;

FIG. 9 is a schematic cross-sectional view taken in central longitudinal plane of FIG. 6;

FIG. 13 is a perspective view of another embodiment of the invention in which a broad area electrode is employed;

FIG. 14 is a side view of the unit shown in FIG. 13;

FIG. 15 is a view from the electrode side of the unit of FIG. 13; and

FIG. 16 is a side view of an alternative electrode or interface conductor which may be used with the basic unit of FIG. 13, and substituted for the electrode shown in FIG. 15.

DETAILED DESCRIPTION OF THE PREFERRED EMBODIMENTS

Figure 1A:
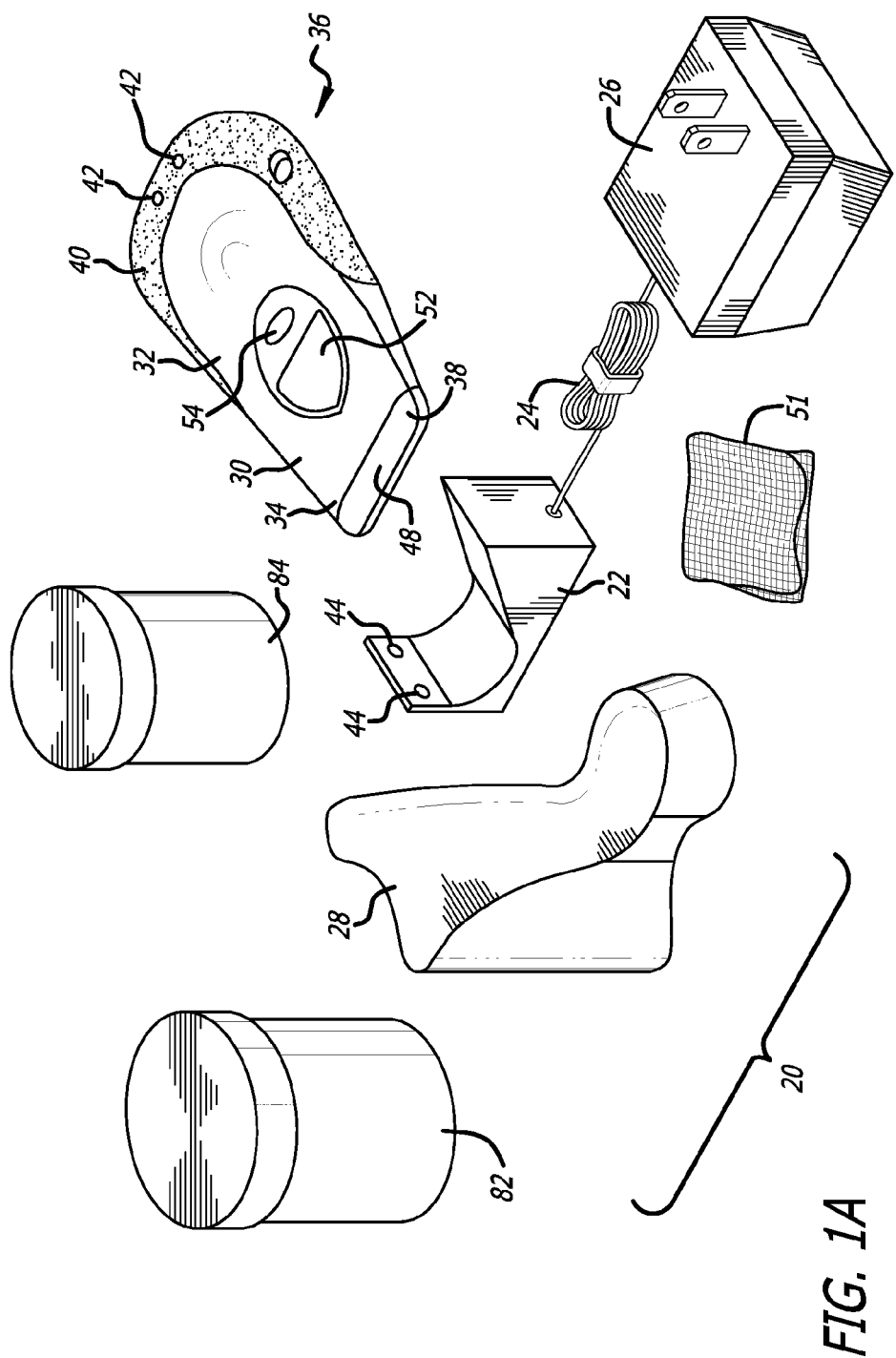
FIG. 1A is a perspective view of a skin/hair conditioning system in accordance with one embodiment of the present invention.

While the specification describes particular embodiments of the present invention, those of ordinary skill can devise variations of the present invention without departing from the inventive concept.

The invention is a method and system of conditioning human skin and hair using a hand-held skin/hair conditioner having interchangeable interface conductors that are contoured to enhance electrical conductivity between the conditioner and a variety of body areas. Each of the interchangeable interface conductors is preferably formed to maximize surface area contact with a variety of body surfaces such as scalp/hair, body skin, and facial skin. In a preferred embodiment, the skin/hair conditioner is formed to fit comfortably and controllably in a user's grasp and includes tactile surfaces to further assist the user's grasp of the skin/hair conditioner under a variety of environments.

Referring more particularly to the drawings, FIG. 1 is a perspective view of a skin/hair conditioning system, shown generally at 20, in accordance with one embodiment of the present invention. In this embodiment, the skin/hair conditioning system 20 includes a recharger assembly 22, 24, 26 and stand 28 for cradling the skin/hair conditioner 30 described in greater detail below. Alternatively, the skin/hair conditioner 30 contains a disposable non-rechargeable battery for a power source. The conditioning system 20 includes a pretreatment 82, a treatment 84, and the skin/hair conditioner 30 having interchangeable interface conductors 48, 50, 60, 70 (respectively FIGS. 1, 2A-2C, 3A-3C, 4A-4C) for use on a variety of body surfaces.

The interface conductors 48, 50, 60, 70 are removably attachable to the skin/hair conditioner 30 such that the user simply selects and attaches a specific interface conductor depending on a particular body surface to operate the skin/ hair conditioner 30. To change operation of the skin/hair conditioner 30 in response to a different body surface, the user detaches the selected interface conductor, selects an appropriate interface conductor for the different body surface, and attaches the selected interface conductor to the skin/hair conditioner 30.

The skin/hair conditioning system 20 may include a porous medium 51 that is interposed between the skin/hair conditioner 30 and a body surface during operation of the skin/hair conditioner. The porous medium enhances efficacy of the pretreatment or treatment preparation as applied to the body surfaces. In particular, the porous medium assists in evenly distributing the pretreatment and treatment preparation while additionally assisting in maintaining moisturization of the preparation. One example of a porous medium is conventional gauze.

The skin/hair conditioner 30 includes a housing 32 having a front end, shown generally at 34, and a finger-engaging surface, shown generally at 36, a front end electrode 38 connected to the front end 34 of the housing 32, a hand-engaging electrode 41 connected to the hand-engaging surface 36 of the housing 32, a power source 72 (FIG. 5) contained within a rear portion 40 the housing 32, an electrical system 170 (FIG. 5) contained within the housing 32 and connected to the power source 172, the hand-engaging electrode 41, and the front end electrode 38, and the aforementioned interface conductor 48, 50, 60, 70. The interface conductor 48, 50, 60, 70 is removably attachable and electrically connectable to the front end electrode 38. Although the interface conductor 48, 50, 60, 70 is described as attachable to the front end electrode 38, the interface conductor and front end electrode 38 may be coupled as a united component 38/48 that is together removably attachable to the skin/hair conditioner 30 at the front end 34 of the housing 32.

The skin/hair conditioner 30 may additionally include an alphanumeric display 52 and a selection switch 54. The display 52 is preferably a liquid crystal display (LCD) that is positioned on the housing 32 and connected to electrical system 170 and the power source 172 such that the electrical system transmits conductor state information via the display 52. The selection switch 54 is positioned on the housing 32 and coupled with the electrical system 70. The switch 54 allows the user to operate the skin/hair conditioner 30 in various modes, described in greater detail below.

As best shown in FIG. 1A, the hand-engaging surface 36 is located on a bottom surface of the housing 32, and the front end 34 is located at an end of the housing 32. On the surface of the housing 32, a rubber grip portion may be provided to enable the user to better grasp the skin/hair conditioner 30. A peripheral rubber seal may also be incorporated with the housing 32 to make the housing watertight.

As previously mentioned, interchangeable interface conductors 48, 50, 60, 70 are removably attachable to the front end electrode 38. Each interface conductor includes a coupling portion connectable to the front end electrode 38 and an interface portion positioned adjacent the coupling portion as best shown FIGS. 2A-2C, 3A-3C, and 4A-4C, and further described below.

Figure 1B:
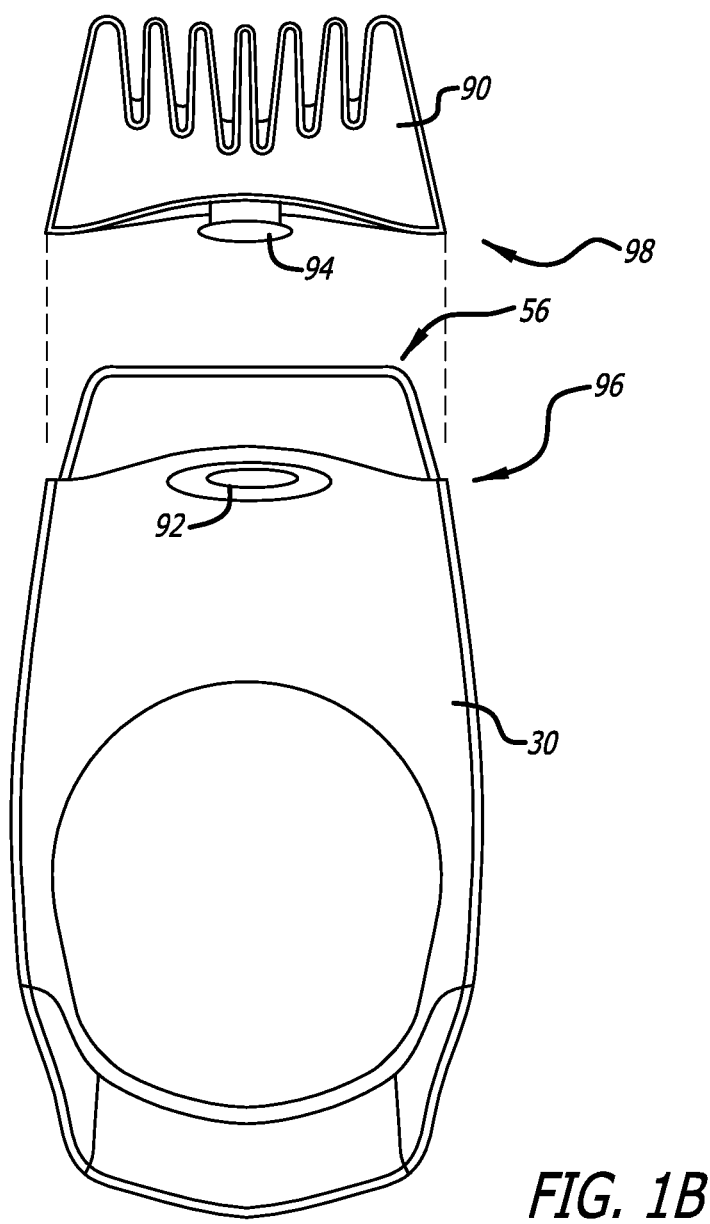
FIG. 1B is a perspective view of the skin/hair conditioner with an interchangeable interface conductor in accordance with the present invention.

FIG. 1B is a perspective view of the skin/hair conditioner 30 with an interchangeable interface conductor 90 in accordance with the present invention. The conditioner 30 also includes a securing device that allows for temporary attachment of the interface conductor to the conditioner 30. The securing device preferably includes an inserting portion and a receiving portion that is formed to mate with the inserting portion. In one embodiment, the inserting portion is formed with the coupling portion of the interface conductor, and the receiving portion that is formed with the front end 34 of the housing 32. Alternatively, the inserting portion is formed with the front end 34 of the housing 32, and the receiving portion is formed with the interface conductor. For example, the securing device may be a tongue and groove configuration in which the tongue extends from the coupling portion of the interface conductor and the groove is formed on the front end 34 of the housing 32. When the interface conductor is attached to the conditioner, the groove receives and temporarily retains the tongue. Another example of the securing device is a depressible latch and slot, shown generally at 56. Those skilled in the relevant art will appreciate that numerous alternative conventional securing mechanisms not described herein may be employed to removably attach the interface conductor to the conditioner 30.

FIG. 2A is a top view of a skin/hair conditioner 30 with a standard interface conductor 50 attached thereto in accordance with one embodiment of the present invention. FIG. 2B is a side view of the skin/hair conditioner 30 shown in FIG. 2A. FIG. 2C is a bottom view of the skin/hair conditioner 30 shown in FIG. 2A. The standard interface conductor 50 is formed for use on facial skin surfaces.

Figure 3C:
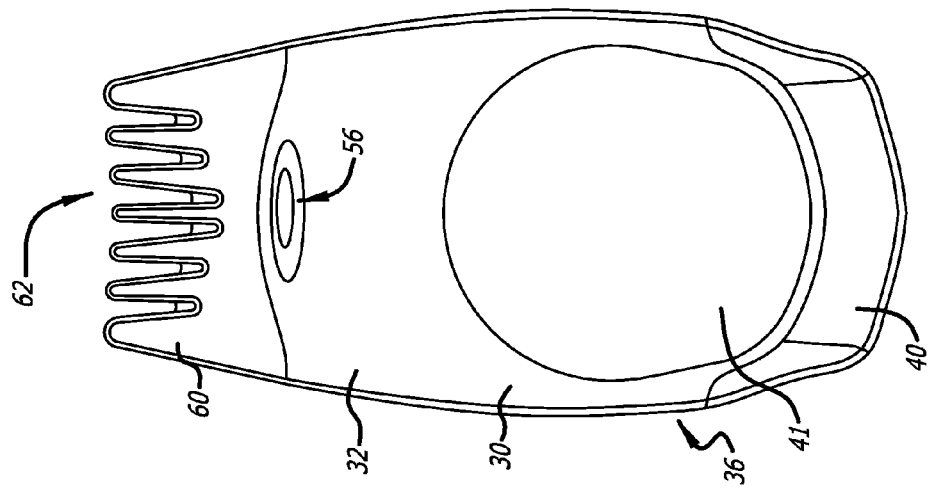
FIG. 3C is a bottom view of the skin/hair conditioner shown in FIG. 3A.
Figure 3B:
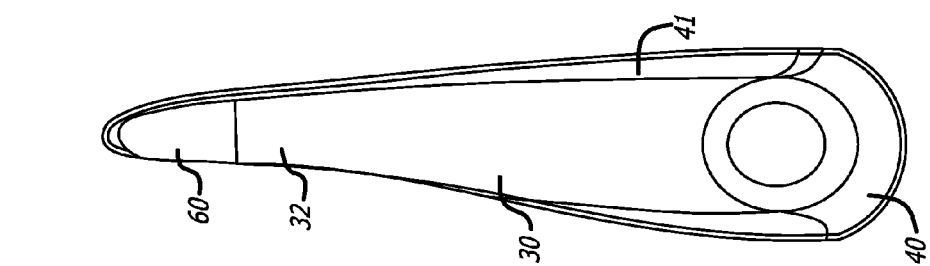
FIG. 3B is a side view of the skin/hair conditioner shown in FIG. 3A.
Figure 3A:
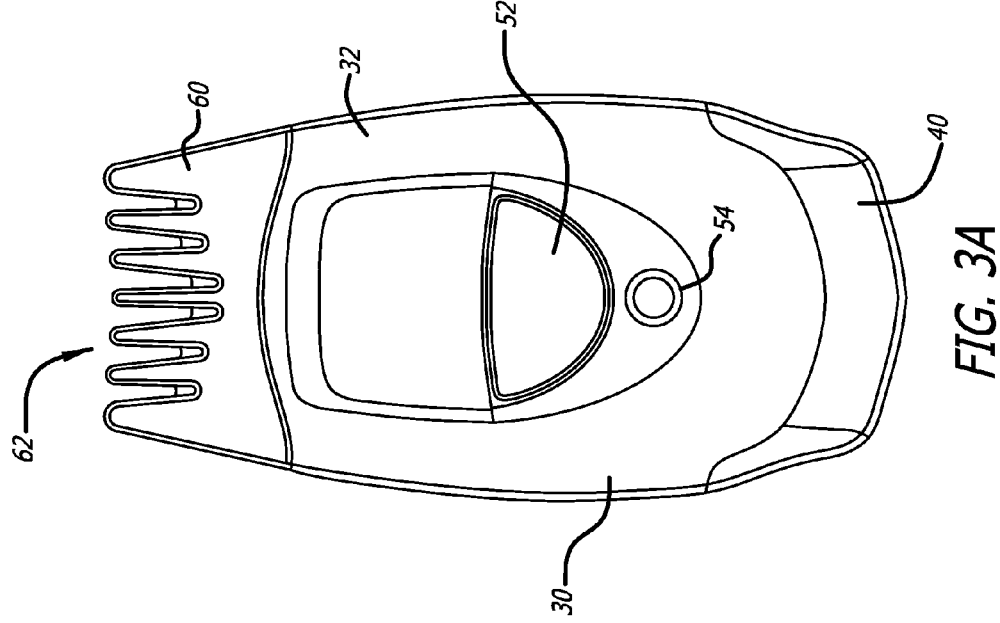
FIG. 3A is a top view of a skin/hair conditioner with a hair interface conductor attached thereto in accordance with one embodiment of the present invention.

FIG. 3A is a top view of a skin/hair conditioner 30 with a hair interface conductor 60 attached thereto in accordance with one embodiment of the present invention. FIG. 3B is a side view of the skin/hair conditioner 30 shown in FIG. 3A. FIG. 3C is a bottom view of the skin/hair conditioner 30 shown in FIG. 3A. The hair interface conductor 60 is formed for use on the user's scalp and hair, and preferably includes teeth formed on the interface portion of the conductor 60, shown generally at 62, that are adapted to maximize contact of the hair interface conductor 60 with the scalp and hair.

Figure 4C:
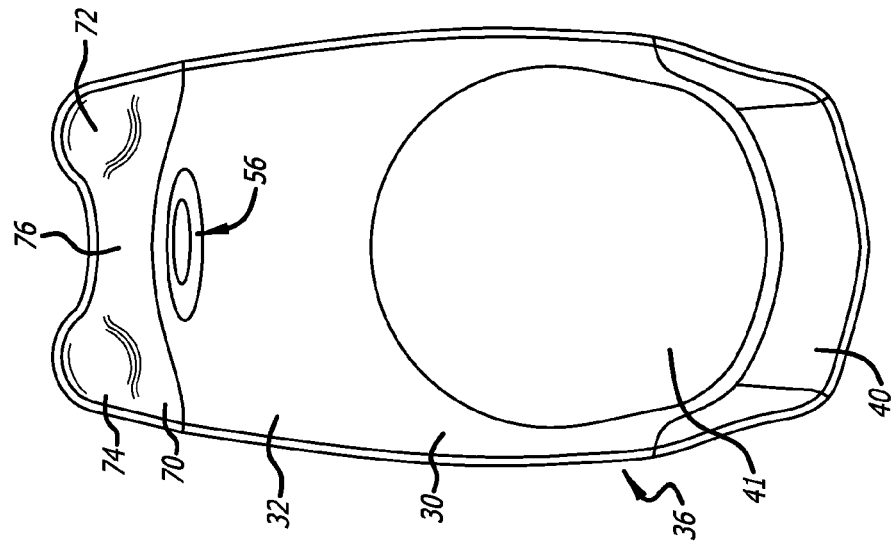
FIG. 4C is a bottom view of the skin/hair conditioner shown in FIG. 4A.
Figure 4B:
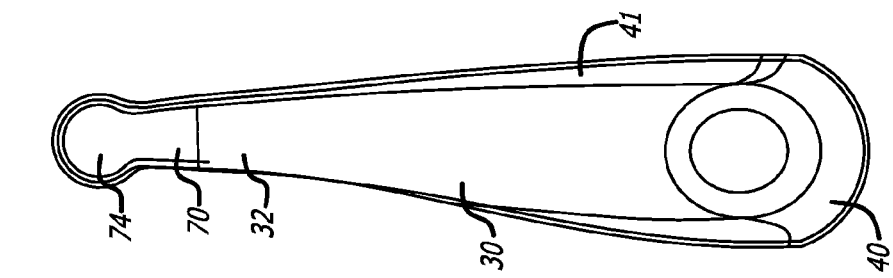
FIG. 4B is a side view of the skin/hair conditioner shown in FIG. 4A.
Figure 4A:
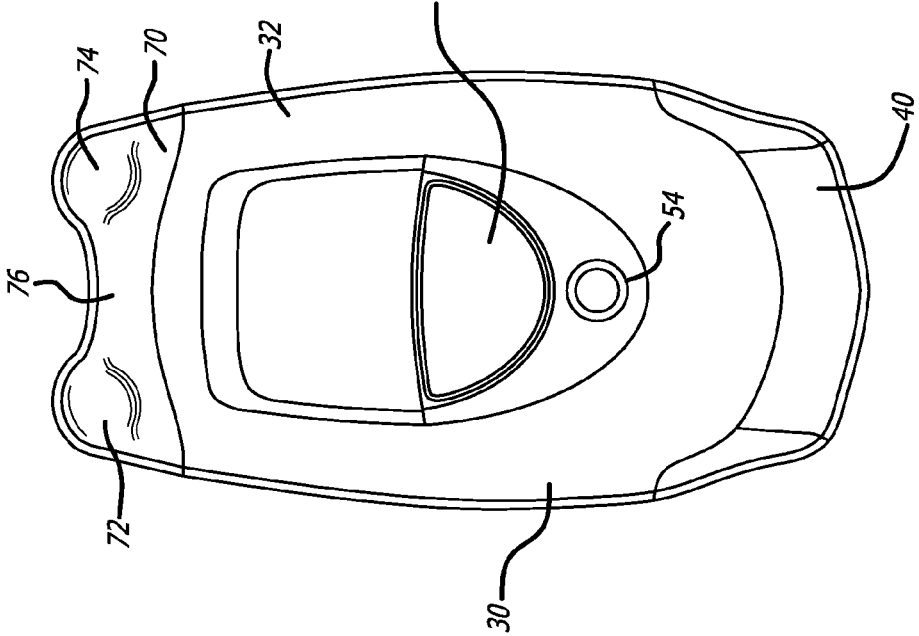
FIG. 4A is a top view of a skin/hair conditioner with a multi-surface interface conductor attached thereto in accordance with one embodiment of the present invention.

FIG. 4A is a top view of a skin/hair conditioner 30 with a multi-surface interface conductor 70 attached thereto in accordance with one embodiment of the present invention. FIG. 4B is a side view of the skin/hair conditioner 30 shown in FIG. 4A. FIG. 4C is a bottom view of the skin/hair conditioner 30 shown in FIG. 4A. The multi-surface interface conductor 70 is formed for use on various body skin surfaces, such as arms, legs, chest, and back. Body skin surfaces tend to vary in contour in comparison with facial surfaces that are relatively flat. In a preferred embodiment, the multi-surface interface conductor 70 includes a pair of round nodules 72, 74 that are separated by a depression 76. The nodules 72, 74 are formed on the interface portion of the conductor 70 to address a variety of skin surface contours on the body and thus provide maximum contact of the conductor 70 against the body skin surfaces.

The interchangeable interface conductors 48, 50, 60, 70, as shown in FIGS. 2A-2C, 3A-3C, and 4A-4C, are preferred embodiments of interface conductors that may be used with the skin/hair conditioner 30. Other conductors having the same coupling portion but differently shaped interface portions are connectable to the front end electrode 38 of the conditioner 30.

The skin/hair conditioner 30 provides two skin treatment modes, including a PRETREAT MODE and a TREAT MODE. The pretreatment process is an anaphoresis process where a negative-to-positive current is used to induce a topical pretreatment preparation having negatively charged ions into the skin/hair to open pores and deeply cleanse/condition the skin/hair. Prior to operating the conditioner 30 in PRETREAT MODE, the user should first thoroughly clean the skin/hair portion where the user wishes to apply the skin treatment, such as the user's face, and then apply the water-based pretreatment to the skin portion. A pH level is used in expressing both acidity and alkalinity on a scale whose values run from 0 to 14 with 7 representing neutrality, numbers less 7 representing increasing acidity, and numbers greater than 7 representing increasing alkalinity. The pretreatment preparation may be alkaline with a preferred pH level of approximately 8. However, the pH level of the pretreatment may be in the general range from about 7 to about 9 or 10. After applying the pretreatment preparation to the skin portion, the user should then pick up the skin/hair conditioner 30 that is currently turned off or in OFF MODE, press the switch 54 to put the conditioner 30 in PRETREAT MODE, and hold the conditioner 30 to the skin portion to be treated such that the interface conductor contacts the skin. As the user applies the conditioner 30 to the skin portion, a negative-to-positive current is applied to the skin.

On the other hand, the treatment process is a cataphoresis process where a positive-to-negative current is used to induce a topical treatment preparation having positively charged ions into the skin/hair to close pores and deeply moisturize/condition the skin/hair. The treatment preparation may be acidic with a preferred pH level of approximately 6. However, the pH level may generally in the range of about 4 or 5 to about 7. Prior to using the skin/hair conditioner 30 in TREAT MODE, the user should have applied the treatment preparation to the skin portion to be treated. Then the user should put the conditioner 30 in TREAT MODE, and apply the conditioner 30 to the skin portion such that the interface conductor contacts the skin. As the user applies the conditioner 30 to the skin portion, a positive-to-negative current is applied to the skin.

Figure 5:
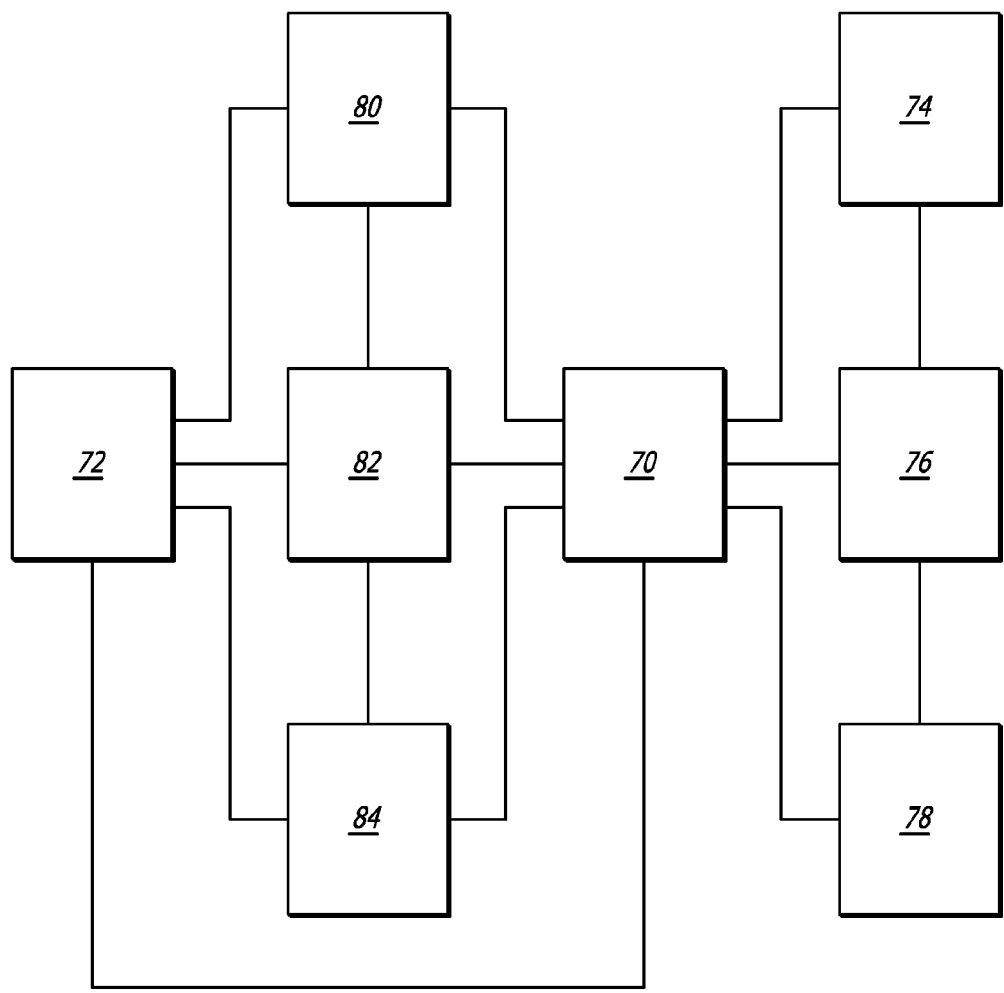
FIG. 5 is a block schematic diagram of an electrical system in accordance with the present invention.

FIG. 5 is a block schematic diagram showing the electrical system 170 in accordance with the present invention. As previously mentioned, the electrical system 170 is connected to the power source 172, the hand-engaging surface electrode 174, the front end electrode 176, and the interchangeable interface conductor 178. Additionally, as previously mentioned, the display 184 is connected to the electrical system 170 and the power source 172 such that the electrical system transmits conductor state information via the display 184. The electrical system 170 controls current supplied to the hand-engaging surface electrode 174 and the front end electrode 176 and includes a printed circuit board (PCB) mounted within the housing 32 of the conditioner 30. The PCB has a microprocessor mounted thereon for executing a software program that interfaces with electronic circuitry to provide various functions or modes of operations of the conditioner 30. The microprocessor, the software program, the electronic circuitry, and the various modes of operations are described in greater detail below. During operation of the skin/hair conditioner 30, an electrical circuit is completed that routes from the conditioner through the front end electrode 38, through the interface conductor (which is moved over the face or other skin/hair treatment area), through the body of the user, and back through the hand-engaging surface electrode 40 to the conditioner.

The microprocessor is preferably fabricated on a single microchip along with readonly memory (ROM) and random-access memory (RAM) associated therewith. In one embodiment, a 4-bit microprocessor is used. However, the data capability of the microprocessor is not critical to the operation of the conditioner, and any conventional microprocessor providing similar functions may generally be used. The microprocessor executes the software program stored in the ROM to interface with other hardware components of the electrical system 170 and provide various functions or modes of operations.

The power source 172 of the skin/hair conditioner 30 is preferably a disposable, nonrechargeable battery. The disposable battery is housed in the rear portion 40 of the housing 32 and may be selected from conventional batteries including, but not limited to, alkaline, carbon zinc, lithium, and nickel metal hydride. Additionally, the microprocessor is connected to a low battery detection circuitry. When the microprocessor detects that the battery is low, the microprocessor informs the user by displaying a blinking legend "LOW BATTERY" on the display 52.

The electrical system also includes a skin detection circuitry and an interface conductor circuitry. When the user properly holds the skin/hair conditioner 30 to the skin portion to be treated, the microprocessor indicates that there is sufficient contact between the skin/hair conditioner 30 and the skin of the user. Depending on the selected interface conductor, the interface conductor circuitry determines a conductor-specific operation of the skin/hair conditioner 30. For example, when the hair interface conductor 60 is coupled to the skin/hair conditioner 30, the interface conductor circuitry confirms that the hair interface conductor 60 is coupled to the skin/hair conditioner 30 and initiates a corresponding mode of operation or sequence of modes of operation.

To assist the user with determining the operation mode or status of the skin/hair conditioner 30, a vibration mechanism 180 and an audio signal generator 182 may be electrically coupled with the microprocessor of the electrical system 170. The vibration mechanism 180 is preferably activated when the skin/hair conditioner 30 in operated in PRETREAT MODE or TREATMENT MODE to alert the user that the conditioner is working. The audio signal generator 182 provides a brief audible tone to indicate to the user a change in operation mode of the skin/hair conditioner 30. For example, the audio signal generator may sound a tone when the PRETREAT MODE is activated. The type or frequency of the tone generated by the audio signal generator is not critical to the operation of the skin/hair conditioner 30, and various types of tones or sequences of tones may be used to indicate a change in status of the skin/hair conditioner 30.

The electrical system also includes a mechanism, a skin resistance circuitry, to sense moisture or resistance on the skin and to feed the result back to the microprocessor. The main principle adopted is that a lower level of moisture or a higher level of resistance results in a higher voltage level in the system. Therefore, the skin resistance circuitry measures the voltage level at key points in the system to determine the level of skin moisture or resistance. Once supplied with information about the skin moisture or resistance, the microprocessor may appropriately adjust the current level to maintain a constant output of power ($P=I^2R$), and thereby avoid shocking users whose skins have a higher level of moisture or resistance.

As stated above, the exemplary skin/hair conditioner 30 provides two skin treatment modes, including PRETREAT MODE and a TREATMENT MODE. Prior to selecting the PRETREAT MODE, the user should first thoroughly clean a skin portion where the user wishes to apply the skin treatment, and then apply the water-based, pretreatment preparation to the skin portion. After applying the pretreatment preparation to the skin portion, the user should then pick up the conditioner 30 that is currently turned off or in OFF MODE, press the switch 54, and hold the conditioner 30 to the skin portion to be treated such that the interface conductor contacts the skin.

The pressing of the switch 54 takes the skin/hair conditioner 30 from the OFF MODE to the PRETREAT MODE. Upon entering PRETREAT MODE, the microprocessor turns on the conditioner 30, sets the current flow and the voltage control to low, establishes the current flow polarity from negative to positive, and indicates to the hardware to step up the voltage. Then the conditioner 30 displays the legend "PRETREAT ANALYZE" on the alphanumeric display 26, resets a timer that is used to monitor a time out interval and application duration, and proceeds to detect the level of skin moisture.

However, if the user fails to properly hold the skin/hair conditioner 30 to the skin portion, the conditioner 30 will turn off after a predetermined time out period. The preferred predetermined time out interval is approximately ten minutes. However, the interval may generally be in the range of about five to fifteen minutes. The purpose of having an automatic time out is to conserve power when the skin/hair conditioner 30 is not in use and to prevent having to replace the battery too frequently.

During the predetermined time-out period, the skin/hair conditioner 30 continuously monitors whether the user properly holds the skin/hair conditioner 30 to the skin portion to be treated, whether the battery is low, whether the recharger assembly 22, 24, 26 is attached, and whether the switch 54 is pressed. Although the recharger assembly 22, 24, 26 is used in conjunction with rechargeable batteries, the recharger assembly 22, 24, 26 may also operate as an AC to DC converted power source for the skin/hair conditioner 30. If the battery is low, the skin/hair conditioner 30 automatically enters LOBATT MODE. In one embodiment using a rechargeable battery, if the battery is not low but the recharger assembly 22, 24, 26 is attached, the skin/hair conditioner 30 is put in CHARGE MODE. If the battery is not low and the switch 54 is pressed, the skin/hair conditioner 30 is put in TREAT MODE.

If the user properly holds the skin/hair conditioner 30 to the skin portion to be treated, the skin/hair conditioner 30 automatically selects one of a plurality of current levels depending upon the level of skin moisture detected. In the preferred embodiment, there are three current levels, including LOW, MEDIUM, or HIGH. The preferred LOW current level is approximately 0.25 mA (milliamp or a thousandth of an amp); the preferred MEDIUM current level is approximately 0.375 mA; and the preferred HIGH current level is approximately 0.5 mA. However, these current levels may be continuously varied and may generally be in the range from about 0.01 mA to about 1.0 mA. Furthermore, the MEDIUM current level is used as the preferred default current level. After the current level is selected, the audio signal generator, such as a buzzer, is sounded once for LOW, twice for MID, and thrice for HIGH.

When the legend "PRETREAT IN PROGRESS" is indicated on the display 52, the user should apply the skin/hair conditioner 30 to the skin portion to be treated by moving the conditioner 30 over all areas of the skin portion for a predetermined application duration. The preferred predetermined application duration is approximately three minutes; however, the application duration may be in the general range of about one to twenty-five minutes. During the predetermined application duration, the conditioner 30 continuously monitors whether the switch 54 is pressed, whether the battery is low, whether the recharger assembly 22, 24, 26 is attached to the conditioner 30, and whether the application duration has expired. If the switch 54 is pressed, the conditioner 30 enters TREAT MODE. If the switch 54 is not pressed and the battery is low, the conditioner 30 enters LOBATT MODE. In the rechargeable battery embodiment, if the switch 54 is not pressed, the battery is not low, and the recharger assembly 22, 24, 26 is attached, the skin/hair conditioner 30 enters CHARGE MODE.

When the predetermined application duration expires, the conditioner 30 enters PRETREAT DONE MODE. In PRETREAT DONE MODE, the skin/hair conditioner 30 first goes into a PAUSE state where the current flow, the voltage control, and the polarity are all set to low. The skin/hair conditioner 30 then sounds the buzzer twice to notify the user that the application duration has expired, and resets a clock that is used to keep track of the time out interval and the application duration. While in PRETREAT DONE MODE, the skin/hair conditioner 30 enters OFF MODE to shut off if the user fails to press the switch 54 within the predetermined time out interval. Also, during the predetermined time out interval, the skin/hair conditioner 30 continuously monitors whether the switch 54 is pressed, whether the battery is low, whether the recharger assembly 22, 24, 26 is attached, and whether the predetermined time out interval has expired. If the switch 54 is not pressed and the battery is low, the skin/hair conditioner 30 enters LOBATT MODE. In the rechargeable battery embodiment, if the switch 54 is not pressed, the battery is not low, and the recharger assembly 22, 24, 26 is attached, the skin/hair conditioner 30 enters CHARGE MODE. If the switch 54 is pressed, the skin/hair conditioner 30 enters TREATMENT MODE.

As previously mentioned above, the moisturizing process is a cataphoresis process where an acid pH treatment is induced into the skin to close pores and deeply moisturize the skin. Prior to using the skin/hair conditioner 30 in TREATMENT MODE, the user should have applied an acidic pH treatment to the skin portion to be treated. Then the user should put the skin/hair conditioner 30 in TREATMENT MODE, and apply the conditioner 30 to the skin portion such that the interface conductor contacts the skin.

When the skin/hair conditioner 30 is put in TREATMENT MODE, the microprocessor turns on the conditioner 30, sets the current flow and the voltage control to low, and establishes the current flow polarity from positive to negative. Furthermore, the skin/hair conditioner 30 displays the legend "TREATMENT ANALYZE" on the alphanumeric display 52, resets the timer which is used to keep track of the time out interval and the application duration, and proceeds to detect the level of skin moisture.

However, if the user fails to properly hold the skin/hair conditioner 30 to the skin portion to be treated, the conditioner 30 turns off after the predetermined time out interval. During the predetermined time out interval, the skin/hair conditioner 30 continuously monitors whether the conditioner 30 is held to the skin portion to be treated, whether the battery is low, whether the recharger assembly 22, 24, 26 is attached, and whether the switch 54 is pressed. If the battery is low, the conditioner 30 automatically enters LOBATT MODE. In the rechargeable embodiment, if the battery is not low and the recharger assembly 22, 24, 26 is attached, the skin/hair conditioner 30 enters CHARGE MODE. If the battery is not low, the recharger assembly 22, 24, 26 is not attached, and the switch 54 is pressed, the skin/hair conditioner 30 enters OFF MODE when the predetermined time out interval expires.

If the user properly holds the skin/hair conditioner 30 to the skin portion to be treated, the conditioner 30 automatically selects one of a plurality of current levels depending upon the level of skin moisture and resistance detected. As noted above, the preferred embodiment has three current levels, including LOW, MEDIUM, or HIGH. Furthermore, the MEDIUM current level is used as the preferred default current level.

When the skin/hair conditioner 30 displays the legend "TREATMENT IN PROGRESS" on the display 52, the user should then apply the skin/hair conditioner 30 to the skin portion to be treated by moving the conditioner 30 over all areas of the skin portion for a predetermined application duration. During the predetermined application duration, the conditioner 30 continuously monitors whether the switch 54 is pressed, whether the battery is low, whether the recharger assembly 22, 24, 26 is attached to the conditioner 30, and whether the application duration has expired. If the switch 54 is pressed, the conditioner 30 enters OFF MODE. If the battery is low, the skin/hair conditioner 30 enters LOBATT MODE. In the rechargeable embodiment, if the battery is not low and the recharger assembly 22, 24, 26 is attached, the conditioner 30 enters CHARGE MODE.

When the predetermined application duration expires, the skin/hair conditioner 30 enters TREATMENT DONE mode. Upon entering the TREATMENT DONE MODE, the skin/hair conditioner 30 first enters a PAUSE state where the current flow, the voltage control, and the polarity are all set to low. While in TREATMENT DONE MODE, the skin/hair conditioner 30 enters OFF MODE to shut off if the user fails to press the switch 54 within the predetermined time out interval. During the predetermined time out interval, the skin/hair conditioner 30 continuously monitors whether the battery is low, whether the recharger assembly 22, 24, 26 is attached, and whether the switch 54 is pressed. If the battery is low, the skin/hair conditioner 30 automatically enters LOBATT MODE. In the rechargeable embodiment, if the battery is not low but the recharger assembly 22, 24, 26 is attached, the skin/hair conditioner 30 automatically enters CHARGE MODE. If the battery is not low, the recharger assembly 22, 24, 26 is not attached, and the switch 54 is pressed, the skin/hair conditioner 30 enters OFF MODE.

All capacitors in the electronic circuitry of the skin/hair conditioner 30 are discharged when the unit 14 is put in OFF MODE. Then the voltage control is set to low, the polarity is set to high, and the voltage is stepped down. Following a delay of approximately 188 MS (milli-second or a thousandth of a second), the skin/hair conditioner 30 is put in an IDLE state where the voltage control, the polarity, and the current level are set to low. A battery clock is then disabled, and the alphanumeric display 52 is blanked. Even in OFF MODE, the conditioner 30 still continuously monitors whether the switch 54 is pressed, whether the battery is low, and whether the recharger assembly 22, 24, 26 is attached. If the switch 54 is pressed, the conditioner 30 switches from OFF MODE to PRETREAT MODE. If the switch 54 is not pressed and the battery is low, the conditioner 30 enters LOBATT MODE. In the rechargeable embodiment, if the switch 54 is not pressed, the battery is not low, and the recharger assembly 22, 24, 26 is attached, the conditioner 30 enters CHARGE MODE.

Upon entering LOBATT MODE, the conditioner 30 is turned off, and the current level, the voltage control, and the polarity are set to low. A blinking legend "LOW BATTERY" appears on the alphanumeric display 52. Then the conditioner 30 monitors whether the recharger assembly 22, 24, 26 is attached. In the rechargeable embodiment, if the recharger assembly 22, 24, 26 is attached, the conditioner 30 enters CHARGE MODE. Upon entering CHARGE MODE, the conditioner 30 is turned off; and the current level, the voltage control, and the polarity are set to low. At this point, if the conditioner 30 detects that the recharger assembly 22, 24, 26 is no longer attached, the conditioner 30 goes into OFF MODE. If the recharger assembly 22, 24, 26 is properly attached, the battery is charged until full. While the battery is being charged, the conditioner 30 displays a blinking legend "CHARGING". When the battery is fully charged, the conditioner 30 displays a blinking legend "DONE CHARGING".

Although the present invention has been described in terms of the preferred embodiment above, numerous modifications and/or additions to the above-described preferred embodiments would be readily apparent to one skilled in the art. Thus, by way of example and not of limitation, the acid pH treatment has a preferred pH level of approximately 6; however, the pH level may generally in the range of about 4 or 5 to about 7. As another example, the alkaline pH pretreatment has a preferred pH level of approximately 8 pH; however, the pH level of the pretreatment may be in the general range of about 7 to about 9 or 10. Also, the predetermined time out interval is preferably about ten minutes; however, the interval may generally be in the range of approximately five to fifteen minutes. Furthermore, the predetermined application duration is preferably about three minutes; however, the duration may generally be in the range of approximately one to six minutes. In addition, the preferred LOW current level is approximately 0.25 mA (milliamp or a thousandth of an amp); the preferred MEDIUM current level is approximately 0.375 mA; and the preferred HIGH current level is approximately 0.5 mA. However, these current levels may be continuously varied and may generally be in the range of about 0.01 mA to 1.0 mA. Accordingly, the present invention is not to be limited to the particular mechanical, electrical, or program steps or embodiments as shown the drawings and described in detail hereinabove.

Recharging Assembly

In one embodiment of the present invention, the skin/hair conditioner 30 has a rechargeable battery for a power source, as previously mentioned above. In this embodiment, the skin/hair conditioning system further includes the aforementioned recharger assembly having a low voltage power supply 26 connected to a recharger mount 22 by wires 24. A rechargeable battery is contained inside the housing 32 around a lower portion of the skin/hair conditioner 30. The battery may be implemented by the use of two commercially available AA size NiCad batteries. These batteries may be permanently connected in series and shrink wrapped.

When the rechargeable batteries for the skin/hair conditioner 30 are low, the skin/hair conditioner 30 is placed on the recharging mount 22 with the power supply 26 plugged into a conventional 115-volt alternating current supply. When the skin/hair conditioner 30 is properly mounted into the recharger mount 22, power is supplied to the conditioner, and the batteries are recharged. Preferably, the skin/hair conditioner 30 includes electrical contacts 42 that engage mating electrical contacts 44 on the recharger mount 22. However, the contacts 42 on the skin/hair conditioner 30 may be retaining terminal screws for holding the two principal portions forming the sealed housing for the conditioner 30 together. Alternatively, separate mating terminals may be employed or juxtaposed coils in the mount 22 and the skin/hair conditioner unit 30 may be used to transfer charging power to the conditioner 30. Additionally, the alphanumeric display 52, which may be a liquid crystal display (LCD), is visible when the skin/hair conditioner 14 is properly positioned on the mount 20. Appearing on the display 52 is a blinking legend "LOW BATTERY" when recharging is needed. During charging, a blinking legend "CHARGING" appears. Following full recharging, a blinking legend "DONE CHARGING" is displayed.

In this embodiment using a rechargeable battery, such as lithium ion and nickel cadmium, the microprocessor can determine whether the battery is charging or is fully charged. Since the microprocessor detects the charge status of the battery, the microprocessor can in turn inform the user of the charge status by displaying either "CHARGING" or "DONE CHARGING" via the alphanumeric display 52.

FIGS. 6 through 9 are drawings directed to one illustrative embodiment of the depressible latch and slot arrangements 56 mentioned hereinabove as applied to the various interface conductors. In FIG. 6 the shoulder 102 separates the front end portion 104 of the unit 30 from the body 106 thereof. The latch member 108 protrudes laterally from the front portion 104 and is slanted to readily mate with the recess 110 of one of the interface conductors of applicators 50 (see FIG. 8A). The other applicators 60 and 70' have corresponding recesses 110' and 110".

In addition, the pins 112, which are spring loaded toward the positions shown in FIG. 6 engage the mating pins 114 of the applicators. The springs 118 bias the pins 112 outward so that the pins 112 have their outer ends flush with the outer surface of front end 104 of the unit 106. The shoulders or flanges 120 provide stops limiting the outward movement of the pins 112. Instead of the spring arrangement shown in FIG. 6, the pins 112 may be broader at the outer ends and engage stop flanges at the outer surface; and may have reduced diameter shafts with the coil springs around these reduced shafts, to accomplish the same result.

When one of the interface conductors or applicators 50, 60 and 70' is mounted onto the front end 104 of unit 30, the pins 114 depress the pins 112 and compress the coil springs 118. Then, when latch 56 is released from slot or recess 110, the springs 118 and pins 112 eject the applicators 50, 60 or 70', or facilitate the removal of the applicators.

As shown in FIG. 9, the latch 108 is at one end of the control member 124, which is pivoted at 126. When the other end 128 is depressed by pressure applied to resilient cover 128, the latch 108 is retracted from recess 110, and the interface conductor or applicator is loosened or ejected.

It is to be understood, of course, that other quick release mechanisms may be employed instead of the specific latch embodiment described hereinabove. Incidentally, with the front end 104 of unit 30 being formed of insulating plastic, the electric current is supplied to the interface conductors 50, 60 and 70 through one or both of the pins 114 which constitute front end electrodes.

Figure 10:
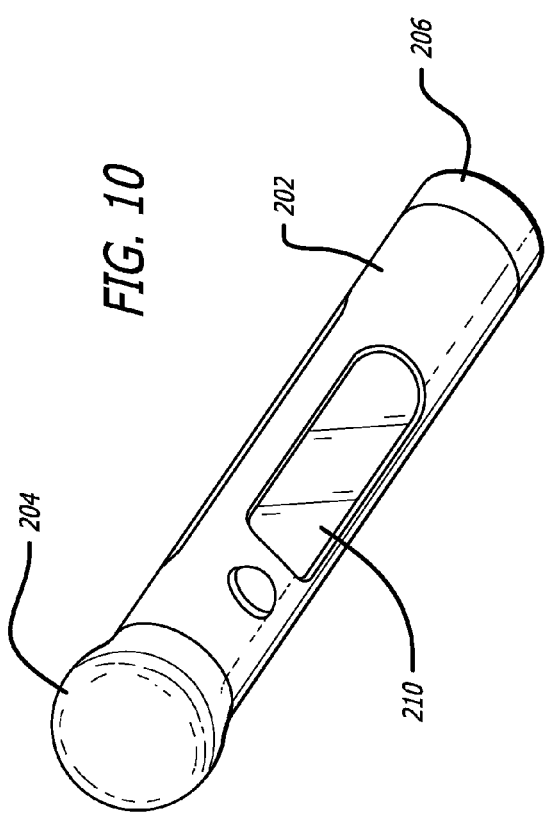
FIG. 10 is a perspective view of an alternative embodiment of the invention.
Figure 11:
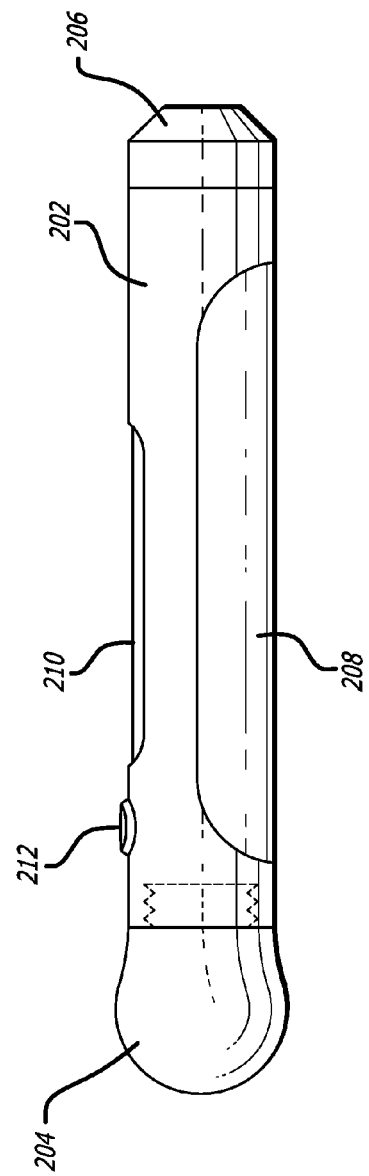
FIG. 11 is a side view of the embodiment of FIG. 10.

Referring now to FIGS. 10 and 11 of the drawings, the basic housing 202 is generally cylindrical in configuration, and has a front electrode or interface conductor 204 which is generally spherical in shape. Batteries may be replaced through the screw-on cap 206.

The hand engaging electrode 208 is on one side of the housing 202, and the visual display 210 is on the other side thereof. The switch 212 is employed to perform the functions of switch 59 in FIGS. 2 and 3 of the drawings.

Figure 12:
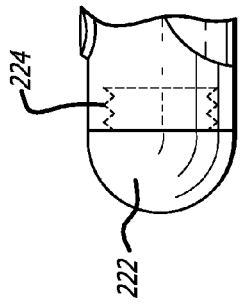
FIG. 12 shows a hemispherical electrode or interface conductor which may be substituted for the interface conductor of FIGS. 10 and 11.

FIG. 12 shows an alternative front end electrode or interface conductor which has a spherical surface but extends for approximately a hemisphere, instead of the greater extent of the electrode 204. The electrode 222 is primarily intended to engage more localized areas such as around the eyes, or on blemishes, while the electrode 204 is intended for other areas such as the lips.

The interface conductors 204 and 222 may be removably secured to the housing 202 in any desired manner, such as by a snap latch, or by relatively coarse threads 224 as shown in FIG. 12. A snap-on latch as shown in FIG. 9 could also be employed, with interfitting or mating edges on the other side of the interface conductors.

FIG. 13 is a perspective view of a compact housing 232 with a knob 234 for easy gripping, so that the configuration may be considered to resemble a door knob. Visible in FIG. 13 are the display 236 and the mode switch 238. The hand engaging electrode 235 extend around the knob 234.

A large, generally flat electrode 240 is shown in FIGS. 14 and 15. Rounded bumps 241 may be provided, or a relative flat electrode as shown at 242 in FIG. 16, may be alternatively and selectively employed. A latching mechanism similar to that of FIG. 9 may be used, with the latch release button 244 shown in FIG. 14. The interface conductors 240 and 242 may have interfitting edges at one end of their oval configurations, and a latch at the other end. A retaining hook or member 243 may be provided at one end of electrode 242 (with a similar hook or electrode 240); and another hook or retaining member 246 is provided at the other end. The release member 244 is coupled to retract a spring biased retaining member when 244 is depressed, in a manner similar to members 108 and 120 of FIG. 9, as noted above.

Incidentally, the embodiments of FIGS. 13-16 are particularly intended for treatment of broad areas of the body such as the thighs and buttocks.

Regarding dimensions, the housings are made to comfortably fit in the users hand or fingers. The basic housing of FIG. 2, for example is about 4½ inches long by 2½ inches wide, by about 1 inch thick. The cylindrical housing of FIGS. 10 and 11 would have a diameter of between about ⅜ inch and about an inch, and a length preferably between about 4 and 6 inches. The oval electrodes of FIGS. 15 and 16 would preferably have a longer dimension of between about two and three inches. However, the foregoing dimensions are merely preferred, and deviations from these preferred dimensions are to be expected.

Concerning construction, the interface conductors are inert and non-porous and have an outer surface which is conductive and corrosion resistant. A preferred embodiment uses an injection molded plastic such as polycarbonate, chrome plated. The interface conductors may also be formed entirely of conductive material either metal or conductive plastic, for examples. The outermost end of each interface conductor is rounded, and this may be defined relative to a plane through the assembly parallel to the central longitudinal axis of the conditioner assembly wherein the cross-sectional configuration is rounded, for smooth engagement with the anatomy of the user. The interface connectors should also have a smoothly curved or rounded extended area, comparable to the area of the front end of the housing.

Concerning one minor matter, it is noted that the interface conductor 70' of FIG. 8C differs slightly from the interface conductor 70 of FIGS. 4A, 4B and 4C in that three rounded nodules are provided instead of the two nodules in the embodiment of FIGS. 4A, 4B and 4C; and the reference numeral 70' is therefore used in reference to FIG. 8C.

Although the skin/hair conditioner 30 and the skin/hair conditioning system 20 are described above with respect to a user, the conditioner 30 and system 20 and the other disclosed embodiments, may be operated by a single user on his or her self and, alternatively, by a second party. For example, the disclosed conditioner systems are ideally suitable for use in salons where a stylist applies the conditioner 30 to an individual. Those of ordinary skill in the art will be aware of other variations that are within the scope of the claimed invention, which is to be measured by the following claims.

The invention claimed is:
1. A hand-held skin/hair conditioner comprising:
a housing having a front end and a hand-engaging surface;
a front end electrode connected to said front end of said housing;
a power source contained within said housing;

an electrical system connected to said power source, and said front electrode for conditioning and controlling current supplied to said front end electrode;

at least first and second interchangeable interface conductors selectively slidably attachable to said front end electrode by a tongue and groove configuration and electrically connectable with said front end electrode, said at least first and second interface conductors having significantly different physical configurations for compatible engagement with different parts of a user's anatomy;

wherein said housing is also configured for ease and convenience in treating various parts of the user's anatomy, and wherein said housing has an elongated flattened configuration.

2. A hand-held skin/hair conditioner comprising:

a housing having a front end and a hand-engaging surface;

a front end electrode connected to said front end of said housing;

a power source contained within said housing;

an electrical system connected to said power source, and said front electrode for conditioning and controlling current supplied to said front end electrode;

at least first and second interchangeable interface conductors selectively threadably attachable to said front end electrode and electrically connectable with said front end electrode, said at least first and second interface conductors having significantly different physical configurations for compatible engagement with different parts of a user's anatomy; and wherein said housing is also configured for ease and convenience in treating various parts of the user's anatomy, and wherein said housing has an elongated, substantially cylindrical configuration.

3. The hand-held skin/hair conditioner according to claim 1, wherein at least one of said interface conductors is generally flat with rounded edges.

4. The hand-held skin/hair conditioner according to claim 1, wherein each of said interface conductors is inert, non-porous, has an outermost end which is smoothly rounded, and has an extended area for engagement with the user's anatomy.

5. The hand-held skin/hair conditioner according to claim 2, wherein each of said interface conductors is inert, non-porous, has an outermost end which is smoothly rounded, and has an extended area for engagement with the user's anatomy.

* * * * *